(12) United States Patent
Zhou

(10) Patent No.: US 7,662,930 B2
(45) Date of Patent: Feb. 16, 2010

(54) POLISHING STEPS USED IN MULTI-STEP PROTEIN PURIFICATION PROCESSES

(75) Inventor: Joe Xin Hua Zhou, Westlake Village, CA (US)

(73) Assignee: AMGEN Inc., Thousand Oaks, CA (US)

( * ) Notice: Subject to any disclaimer, the term of this patent is extended or adjusted under 35 U.S.C. 154(b) by 67 days.

(21) Appl. No.: 11/635,800

(22) Filed: Dec. 6, 2006

(65) Prior Publication Data

US 2007/0167612 A1 Jul. 19, 2007

Related U.S. Application Data

(60) Provisional application No. 60/742,839, filed on Dec. 6, 2005.

(51) Int. Cl.
- A61K 39/395 (2006.01)
- C07K 16/00 (2006.01)
- C07K 1/18 (2006.01)
- C07K 1/34 (2006.01)
- C07K 1/36 (2006.01)

(52) U.S. Cl. ............ 530/390.1; 424/176.1; 424/177.1; 530/390.5; 530/414; 530/416; 530/417

(58) Field of Classification Search .................. None
See application file for complete search history.

(56) References Cited

U.S. PATENT DOCUMENTS

| | | | |
|---|---|---|---|
| 4,780,407 A | * | 10/1988 | Strosberg et al. ......... 424/150.1 |
| 5,110,913 A | * | 5/1992 | Coan et al. ............ 530/388.23 |
| 5,126,130 A | * | 6/1992 | Lussenhop et al. ....... 424/147.1 |
| 6,281,336 B1 | * | 8/2001 | Laursen et al. .......... 530/390.1 |
| 2003/0050450 A1 | | 3/2003 | Coffman et al. |
| 2004/0092719 A1 | | 5/2004 | Birck-Wilson et al. |
| 2004/0138426 A1 | | 7/2004 | Blank et al. |

FOREIGN PATENT DOCUMENTS

EP  0 351 789  * 1/1990

(Continued)

OTHER PUBLICATIONS

Josic et al, Food Technol. Biotechnol., 39 (3), 215-226, 2001.*

(Continued)

*Primary Examiner*—David A Saunders
(74) *Attorney, Agent, or Firm*—John A. Lamerdin

(57) ABSTRACT

Various embodiments of the present invention are directed to multi-step systems and methods for target-molecule purification that employ column-chromatography-based and/or membrane-filtration-based polishing steps. In one described embodiment of the present invention, a target-protein-containing eluate having a high residual salt concentration is collected from a first chromatography column prepared with an affinity-chromatography resin, loaded onto a second chromatography column prepared with a cation-exchange resin, and eluted from the second cation-exchange column using a buffer in which a time-dependent pH gradient is established. In another described embodiment of the present invention, a partially purified target-protein-containing eluate is collected from a chromatography column and further purified by passing the target-protein-containing eluate through a salt-tolerant anion exchanger.

8 Claims, 2 Drawing Sheets

FOREIGN PATENT DOCUMENTS

WO       WO98/56808       12/1998

OTHER PUBLICATIONS

Knudsen et al, Journal of Chromatography A, 907, 145-154, 2001.*

Gagnon et al "Purification Tools for Monoclonal Antibodies", Validated Biosystems, 1996, Chap. 4.*

Mhatre, R., et al., "Purification of antibody Fab fragments by cation-exchange chromatography and pH gradient elution", Journal of Chromatography, (1995) 225-231.

Feng Li, et al. "Current therapeutic antibody production and process optimization" Bioprocessing Journal, Sep. 1, 2005 pp. 23-30.

Joe X. Zhou et al., "Membrane chromatography as a robust purification system for large-scale antibody production" Bioprocess International, Sep. 1, 2005 pp. 32-37.

Zhou, J.X. et al., "Basic concepts in Q membrane chromatography for large-scale antibody production" Biotechnology Progress Mar./Apr. 2006 American Chemical Society US., vol. 22, No. 2, Mar. 2006 pp. 341-349.

* cited by examiner

POLISHING STEPS USED IN MULTI-STEP PROTEIN PURIFICATION PROCESSES

CROSS-REFERENCE TO RELATED APPLICATION

This application claims the benefit of U.S. Provisional Application No. 60/742,839, filed Dec. 6, 2005.

TECHNICAL FIELD

The present invention is related to protein purification and, in particular, to protein purification processes that employ column chromatography and/or membrane filtration polishing steps.

BACKGROUND OF THE INVENTION

Column chromatography is a commonly used technique for separation and purification of particular types of molecules from complex sample solutions and complex sample mixtures that include solutes and suspended or partially solvated chemical entities, such as membrane fragments. A chromatography column is prepared by suspending a resin in a buffer solution to form a resin slurry, and then packing the resin slurry within a chromatography tube to form a matrix within the chromatography tube by following a packing procedure, or packing mode. The matrix constitutes the solid phase or stationary phase within the chromatography column. A complex solution that contains one or more types of molecules to be purified, each type referred to as a "target molecule," is loaded onto the chromatography column in which buffer conditions are established to promote separation of the one or more target molecules from the complex solution. A buffer solution, mobile phase, or eluant solution is then directed through the chromatography column to move desired target molecules and undesired sample-solution components through the chromatography column. Different types of solutes move through the chromatography column at different rates, depending on their different mobilities in, and different affinities for, the mobile phase and the stationary phase, resulting in separation of the one or more target molecules from solutes and suspended entities present in the original sample solution. Solutions containing the one or more target molecules, referred to as "eluates," are subsequently eluted from the chromatography column.

A chromatography column is generally incorporated within a chromatography system that includes one or more pumps, eluate collectors, and detectors. Column chromatography systems are frequently used for purifying biomolecules, including proteins and other biopolymers, from complex solutions and mixtures, such as, for example, purifying recombinant proteins from cell lysates and cell filtrates. After a target molecule has been partially purified by an initial column-chromatography step and collected in an eluate pool, the partially purified target molecule is often subjected to further purification steps, generally referred to as "polishing steps."

Although column chromatography is commonly used to purify various target molecules, certain problems are frequently encountered. It can be difficult to efficiently prepare an eluate containing a target molecule for subsequent polishing steps. In certain cases, the eluate contains a high, residual salt concentration that makes the eluate unsuitable for a next polishing step. In these cases, a buffer may be added to dilute the eluate, resulting in an increased the cost and slowing of the purification process. Researchers, pharmaceutical manufacturers, chromatography-column and matrix manufacturers and vendors, and users of chromatography-based purification methods have recognized the need for improved polishing steps for use in multi-step purification processes.

SUMMARY OF THE INVENTION

Various embodiments of the present invention are directed to multi-step systems and methods for target-molecule separation and purification that employ column-chromatography-based and/or membrane-filtration-based polishing steps. In one described embodiment of the present invention, a target-protein-containing eluate having a high residual salt concentration is collected from a first chromatography column prepared with an affinity-chromatography resin, loaded onto a second chromatography column prepared with a cation-exchange resin, and eluted from the second cation-exchange chromatography column using a buffer in which a time-dependent or eluant-volume-dependent pH gradient is established. In another described embodiment of the present invention, a partially purified target-protein-containing eluate is collected from a chromatography column and further purified by passing the target-protein-containing eluate through a salt-tolerant anion exchanger.

DETAILED DESCRIPTION

Figure 1:
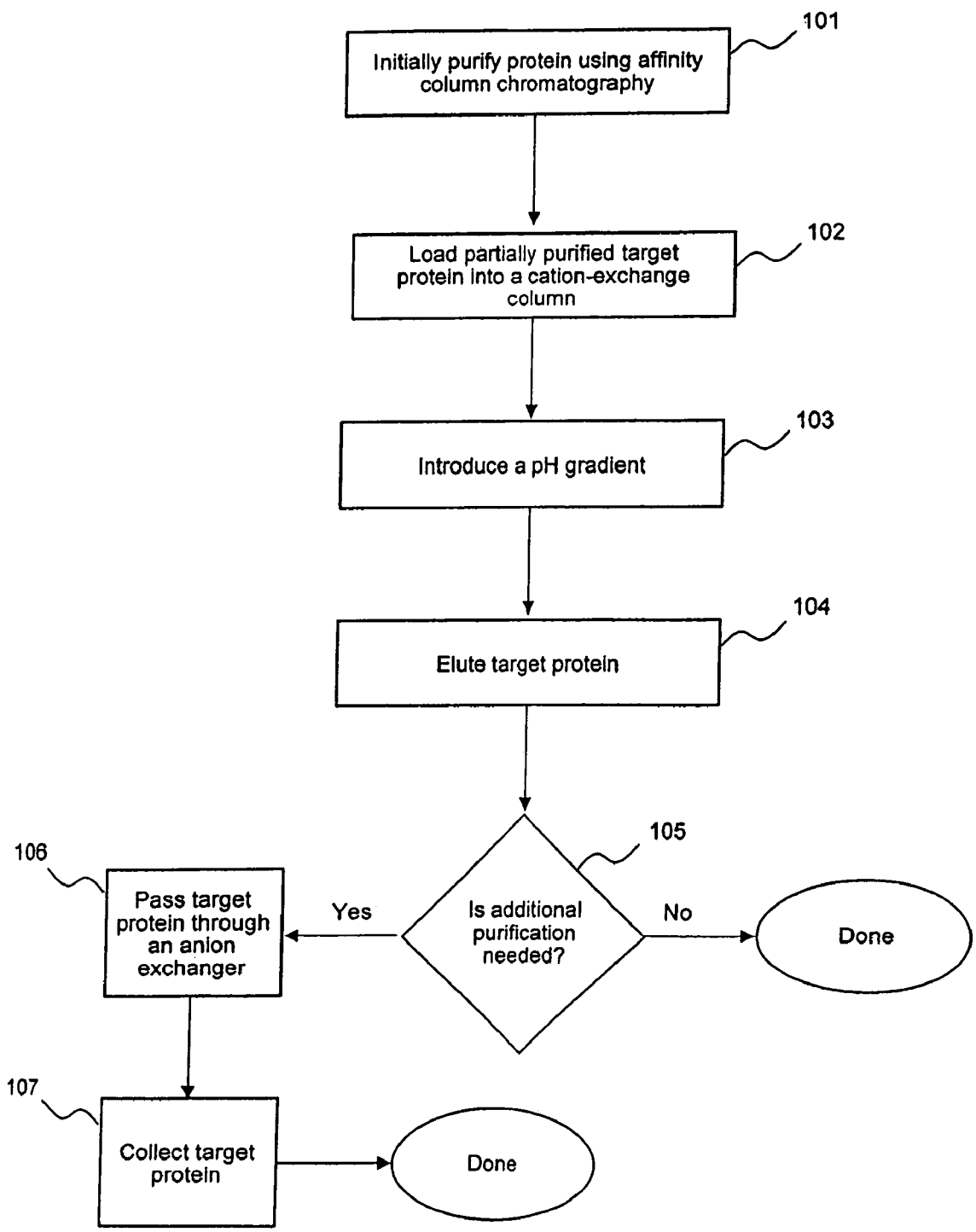
FIG. 1 is a flow diagram that describes a method for purifying a target protein using sequential purification steps that includes application of several embodiments of the present invention.

Various embodiments of the present invention are directed to multi-step target-molecule purification systems that include chromatography-based and/or membrane-filtration-based polishing steps. Described embodiments of the present invention may be directed to separating target proteins, including recombinant monoclonal antibodies, from complex solutions that include host-cell proteins, viral particles, and other impurities. These embodiments are described, below, following description of a multi-step-purification-process context in which embodiments of the present invention may be applied.

Multi-Step-Purification-Process Context

A chromatography column may be used for any of many different liquid chromatographic processes, including ion-exchange chromatography, size-exclusion chromatography, hydrophobic interaction chromatography, and affinity chromatography. In ion-exchange chromatography, a target molecule is separated from a complex solution or mixture based on electrostatic forces between charged functional groups of target molecules and charged functional groups of the chromatography-column matrix. Cation-exchange resins have negatively charged functional groups that attract positively charged functional groups of target molecules, and anion-exchange resins have positively charged functional groups that attract negatively charged functional groups of target molecules. Molecules bound through electrostatic forces to the matrix can be eluted by increasing the ionic strength of the buffer solution within the chromatography column over time.

In size-exclusion chromatography, a target molecule is separated from a complex solution or mixture based on the target molecule's size-related exclusion from the interior regions of spherical beads that make up the matrix. Progress through the chromatography column of smaller molecules that are capable of diffusing into the beads is slowed with respect to the target molecule. In hydrophobic interaction chromatography, a target molecule is separated from a complex solution or mixture based on the hydrophobicity of the target molecule. A complex solution containing the target molecule is applied to a chromatography column equilibrated with a high salt buffer that facilitates binding of the target molecule to the resin. A salt-gradient mobile phase with decreasing ionic strength is then introduced into the chromatography column to release bound target molecules from the matrix. Alternatively, hydrophobic interaction chromatography may separate a monomeric target molecule from a complex solution or mixture by binding hydrophobic impurities, including inactive dimers and aggregates of the target molecule, while permitting monomeric target molecules to flow through the chromatography column relatively unimpeded. In affinity chromatography, a target molecule, such as an antibody, is separated from a complex solution based on the affinity of the target molecule for a ligand or ligand-binding entity that is covalently bound to the matrix. Molecules in the complex solution or mixture with weak affinity, or lacking affinity, for the ligand or ligand-binding entity flow through the chromatography column unimpeded, leaving the target molecule bound to the matrix. The target molecule can then be eluted from the chromatography column by altering buffer conditions to decrease the affinity of the target molecule for the ligand or ligand-binding entity.

Protein A is a ~41 kDa protein from *Staphylococcus aureas* that binds with high affinity (~$10^{-8}$ M-$10^{-12}$ M to human IgG) to the $C_H2/C_H3$ domain of the $F_c$ regions of antibodies and is therefore commonly immobilized within an affinity-chromatography matrix for purifying target antibodies. Due to the biochemical properties of protein A, including a lack of disulfide bond linkages, protein A is very stable and can be used with high salt conditions and/or denaturants, such as 10 M urea, 6 M guanidine, and 80 mM dithiothreitol. Protein-A affinity chromatography is often used for purification of monoclonal antibodies and fusion proteins containing the antibody constant fragment $F_c$. About 98% of process impurities, including viral particles, can be removed by protein-A affinity column chromatography in a single step, with high product yields.

There are many commercially available protein-A affinity chromatography resins that may be used for antibody purification, including ProSep® controlled-pore glass resins produced by Millipore and MabSelect™, cross-linked agarose resin products produced by Amersham Biosciences, and other types of protein-A affinity chromatography resins, including gel-based resins and silica-based resins. The different types of protein-A affinity chromatography resins have different characteristics and properties, and chromatography columns prepared with a particular type of protein-A affinity chromatography resin may be more suitable than chromatography columns prepared with other types of protein-A affinity chromatography resins for purification of particular target molecules under particular conditions.

Protein-A affinity column chromatography may be used as a first step, sometimes referred to as an initial purification step, or "capture step," of a multi-step purification process. An example of a multi-step purification process includes a capture step and one or more polishing steps. The capture step may include adsorbing the protein from a complex solution or complex mixture to protein A immobilized on a solid phase, removing contaminants by washing the solid phase with a wash buffer, and recovering the target protein from the solid phase with an elution buffer. The elution buffer is designed to introduce conditions that interfere with protein-A/$F_c$ binding, such as lowering the pH within the column matrix to a point at which $F_c$ no longer binds to protein A. The capture step may concentrate the target protein. The effectiveness of the capture step may be assessed based on the speed of the chromatography process, the degree of separation of the target protein from undesired solutes and suspended entities, and the load capacity of the chromatography column. Chromatography resins with high load capacities and good flow properties may be particularly well suited for capture steps.

The polishing steps may separate the target protein that has been concentrated and partially purified in the capture step from remaining impurities. The polishing steps may be useful for removing impurities that have relatively closely related chromatographic properties and that eluted together with the target protein during the capture step. Flow rates and load volumes of the polishing steps may be decreased in order to improve resolution. The polishing steps may be useful for removing product-related contaminants, such as aggregates, and trace amounts of process-related contaminants, such as viral particles, from the target protein-containing eluate, as well as for adjusting buffer conditions in preparation for subsequent processing steps.

Described Embodiments of the Present Invention

In various embodiments of the present invention, anion-exchange processes and cation-exchange processes may be used in one or more polishing steps following a protein-A-affinity-chromatography-based purification step. Anion-exchange processes may employ an anion-exchange chromatography column prepared with a poured, hydrated-bead anion-exchange resin. Alternatively, anion-exchange processes may employ a solid, microporous anion-exchange filter membrane. The term "anion exchanger" is subsequently used to refer to both anion-exchange chromatography columns and filter membranes. Cation exchange processes may employ a chromatography column prepared with a cation-exchange chromatography resin. Anion-exchange and cation-exchange processes may be specifically tailored for a given multi-step-purification-process application by optimizing, for example, various parameters, including processing time, product throughput, buffer ionic concentrations, buffer pH, and buffer volume, to improve the productivity and efficiency of the polishing step or steps in which the anion-exchange and cation-exchange processes are employed. Limiting the amount of buffer used in a polishing process may be beneficial by increasing target protein throughput and may result in substantially decreased processing times.

Polishing steps following a protein-A-affinity-column-chromatography capture step may further remove unfolded and aggregated forms of an $F_c$-containing target molecule and may facilitate viral and DNA clearance. Unfolded and aggregated forms of the $F_c$-containing target proteins that survive purification and end up in therapeutic preparations may elicit production of neutralizing antibodies may spur immune reactions against the $F_c$-containing target protein in patients to which the therapeutic preparations are administered. Furthermore, unfolded and aggregated forms of $F_c$-containing target proteins generally do not produced desired, therapeutic effects, and thus diminish the overall potency of therapeutic preparations based on purified $F_c$-containing target proteins. Polishing steps may additionally remove residual viral particles, DNA, and various host impurities, such as Chinese hamster ovary cell protein ("CHOP"), present in an eluate collected in a previous capture step. A polishing step may additionally serve to dilute the ionic concentration of, or change the pH of, an eluate collected in a previous capture step, to prepare the eluate for further processing in subsequent purification steps, including a subsequent column-chromatography purification step.

FIG. 1 is a flow diagram that describes a method for purifying a target protein using sequential purification steps that includes application of several embodiments of the present invention. In step 101, a target protein is initially purified by elution from an affinity chromatography column in a capture step. In one embodiment of the present invention, the affinity chromatography column is prepared with a protein-A-based affinity-chromatography resin for purification of an $F_c$-containing target protein.

Steps 102-103 together compose a first polishing step. The first polishing step is used to remove residual impurities following the affinity-column purification step. In some cases, the impurities typically removed by cation-exchange chromatography include target protein variants produced by amidation, oxidation, truncation, and dimerization or higher-order aggregation of the target protein. Cation-exchange chromatography may remove up to about 80% of remaining CHOP, much of the residual DNA and RNA, residual endotoxins, and residual pigments.

In step 102, the eluate pool containing the target protein that has been initially purified by affinity chromatography in step 101 is loaded onto a second chromatography column. In one embodiment of the present invention, the initially purified eluate pool has a pH of about 5 and a conductivity less than about 5 mS/cm. In the described embodiment of the present invention, the second chromatography column is a cation-exchange chromatography column. A second-step chromatography column for may be prepared, for example, with a Fractogel®V COO⁻ cation-exchange-chromatography resin produced by Merck.

Elution of target protein from a cation-exchange chromatography column often involves applying a buffer prepared to have a time-dependent or volume-dependent salt gradient. Utilizing a salt-gradient buffer for eluting a target protein from the solid phase of a cation-exchange chromatography column may, in some cases, provide desirable separation between the target protein and impurities. However, a significant drawback in some cation-exchange-based purification processes is that the use of a salt gradient may cause the collected eluate pool to have a relatively high ionic strength, or salt concentration. Solutions with high conductivities may be unsuitable for subsequent polishing steps without first decreasing the ionic strength of the collected eluate pool. Dilution of the resulting eluate pool is commonly employed to lower the ionic strength of the eluate pool. Therefore, utilizing a salt gradient during a polishing step may result in the need to dilute the collected eluate pool, which substantially increases the total buffer volume used, and which, in turn, increases the time expended for loading the eluate onto a chromatography column in a subsequent polishing step and therefore increases the overall cost of the purification process.

In the described embodiment of the present invention, the target protein is eluted from a cation-exchange chromatography column using a pH gradient rather than, or in addition to, a salt or buffer gradient. Eluting a target protein from a cation-exchange chromatography column using a pH gradient may minimize the amount of additional buffer used to adjust the pH or conductivity prior to a subsequent polishing step. The pH gradient employed to elute the target protein may be a linear gradient or a stepped gradient.

In step 103, two different buffer solutions, each with a different pH, are mixed in proportions that vary, over time, to produce a linear, time-dependent or volume-dependent pH-gradient buffer that is subsequently used to elute the target protein from the second chromatography column. In alternative embodiments of the present invention, stepwise pH gradients may be used, and in other embodiments of the present invention, non-linear, continuous gradients may be employed. In step 104, the target protein is eluted from the second chromatography column. In one embodiment of the present invention, the elution buffer initially comprises a 30 mM sodium acetate solution at a pH of 5 and, over 13 column volumes of eluant passing through the chromatography column, the sodium acetate concentration rises to 190 mM and the pH rises to 6. In general, relatively narrow pH gradients are desirable, including gradients of less than or equal to 0.5 pH units, gradients of less than or equal to 1 pH unit, and gradients of less than or equal to 2 pH units. The midpoint of the pH gradient is selected to achieve best separation of target molecule from residual impurities, and best recovery of target molecules from the chromatography column. Midpoint pH values may range from pH 4 to pH 7, depending on the target molecules, chromatography column matrix, eluant solution, and other parameters. The separation and recovery characteristics are less affected by the time or eluant-solution volume over which the gradient is established. However, the volume of the fraction of eluant solution containing target molecules increases with increasing eluant-solution volume over which the gradient is established, and so steeper gradients are preferred to avoid one or more additional pool-concentration steps.

When it is determined, in step 105, that no further purification of the target protein is needed, the purification process is complete. Otherwise, in a second polishing step comprising steps 106-107, the target-protein-containing eluate collected from the second chromatography column in the first polishing step is passed through an anion exchanger and the further purified target protein is collected. One family of anion exchangers used in various embodiments of the present invention, referred to as "Q-anion exchangers," includes Q membranes and Q chromatography columns. Q membranes and Q chromatography resins operate as basic anion-exchange adsorbers, and are based on quaternary ammonium salts. Q membranes have large surface to volume ratios, and comprise a thin, microporous adsorptive layer bound to a cellulose matrix. A Sartobind® Q membrane may be employed as the Q membrane in certain embodiments of the present invention, and a chromatography column prepared with Q Sepharose Fast Flow resin, produced by GE Healthcare, formerly Amersham Biosciences, may be employed as a Q chromatography column in other embodiments of the present invention. Since many of the impurities, including host cell protein, DNA, and unbound protein A, occur at concentrations below the limit of detection following cation-exchange chromatography, an anion exchanger may be used to filter residual viral contaminants following the cation-exchange step in which most host cell protein, DNA, and unbound protein A is removed.

In one embodiment of the present invention, a Q membrane may be directly loaded with the eluate collected from a cation-exchange chromatography column, following an about one-fold dilution, having a conductivity of about 3.5-4.5 mS/cm after being titrated to a pH of about 7.2. A Q membrane is generally used once and then disposed, therefore eliminating a cleaning validation step from the anion-exchanger-polishing protocol. In addition, using a Q membrane may eliminate other steps that are typically required when using an anion-exchange chromatography column, such as (1) column lifetime studies, (2) resin carryover development studies, (3) column storage valuation studies, and (4) column packing studies. The ability to load a cation-exchange-column eluate either directly, or after only an about one-fold dilution, onto a Q membrane, rather than diluting the eluate three-to-four-fold, as typically required when eluting a target protein using a salt gradient and resolving the eluate using anion-exchange column chromatography, may decrease the processing time of the polishing steps by an entire day.

In many embodiments of the present invention, the Q membrane comprises multiple, stacked, separate Q-membranes contained within a cell. In many embodiments of the present invention, a flow-through ("FT") Q-membrane ("QM") polishing step is employed, in which an antibody-containing solution is passed through the multi-layer Q-membrane cell at relatively high flow rates, with passage of undesirable, relatively large host-cell proteins, DNA, RNA, intact viruses, and endotoxins restricted by the Q membrane, while smaller antibody molecules readily pass through the Q-membrane cell for downstream collection. For example, a Sartobind Q membrane has pore sizes of 3-5 μm, a thickness of 0.0275 cm, and is employed in a 15-layer cell. Linear flow rates of 600 cm/h can be achieved by FT QM polishing, as compared with 200 cm/h for a Q-Sepharose-Fast-Flow column-anion-exchange-chromatography polishing step. A Q-membrane cell can provide a process capacity of greater than 3600 gm antibody/m$^2$ Q membrane, and viral log reduction greater than 5.0 for certain model viruses used for evaluation of FT QM polishing. Flow rates and operational backpressure are inversely dependent on solution viscosity, in turn dependent of solution temperature, solution pH, solution conductivity, and antibody concentration. Higher temperatures produce lower viscosities, as do solution pH values different from the pI of the antibody that is purified by the process and moderate to high solution conductivities. An FT QM polishing step can provide 98% to 100% native-conformation, uncomplexed antibody recovery, using 5% of the solution volume needed for a column-anion-exchange-chromatography polishing step.

When a variation of the first embodiment of the present invention was tested experimentally, using a Fractogel COO$^-$ cation-exchange chromatography column in a first polishing step, high product throughput and high purity of a target antibody were observed. Use of a pH gradient resulted in a better target protein resolution than use of a salt gradient elution. The volume of the target-protein eluate collected from a cation-exchange column prepared using a pH gradient was about 40%-50% less then the pool size of the eluate from a cation-exchange chromatography column prepared using a salt gradient. When a linear gradient elution was compared to a stepwise gradient elution, it was observed that the linear gradient elution more readily removed impurities, such as target-protein aggregates.

Example 1

Figure 2:
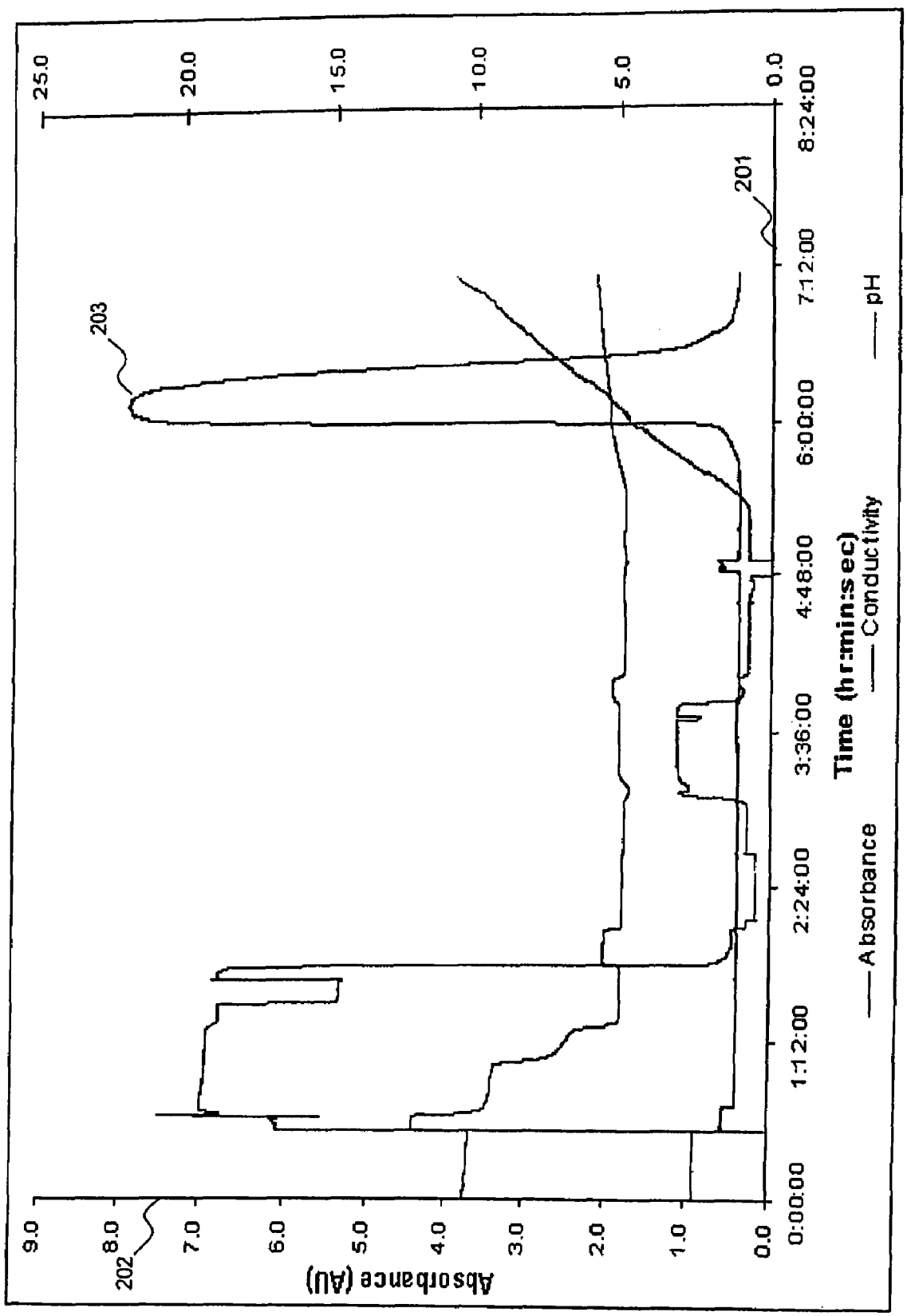
FIG. 2 illustrates a protein-concentration-versus-time plot of a target protein eluted from a cation-exchange chromatography column.

In order to determine whether elution of a target protein from a cation-exchange chromatography column using a buffer with a time-dependent pH gradient is effective in a polishing step of a commercial purification process, a chromatography column with a diameter of 30 cm and a height of 26.5 cm was prepared using a Fractogel COO$^-$ chromatography resin. The calculated binding capacity of the chromatography column was 42.7 g/L and the eluate pool volume loaded onto the Fractogel chromatography column was 4.22 column volumes. An eluate from a protein-A affinity chromatography column containing an antibody target molecule was loaded onto the Fractogel chromatography column and eluted by use of buffer with a linear, time-dependent pH gradient. FIG. 2 illustrates a protein-concentration-versus-time plot of a target protein eluted from a cation-exchange chromatography column. Eluted protein concentration was calculated by measuring UV light absorbance at 280 nm. In FIG. 2, the x-axis 201 represents the peak retention time, and the y-axis 202 represents the UV absorbance in the eluate. The target antibody elution peak 203 shows a robust and generally even distribution, thus supporting the use of a cation-exchange chromatography column in a polishing step following a protein-A-affinity-chromatography column-chromatography step in a multi-step purification. The protein recovery rate was calculated to be about 96.5% and the pH gradient successfully separated multimer aggregates from the monomeric target protein.

Example 2

In order to compare the effectiveness of a Q membrane and a Q chromatography column used as anion exchangers following sequential column-chromatography-based purification steps used to purify a target protein, duplicate samples of a target protein eluate were prepared by collecting target-protein-containing eluate from a cation-exchange chromatography column used in a second purification step following an initial affinity chromatography step. Following elution from the cation-exchange chromatography column, the pH of the eluent pool was about 5.5 and the conductivity was between 6.7 and 6.8 mS/cm. The cation-exchange chromatography column eluant was adjusted to a pH of about 7.2 with Tris base. As shown in Table 1, the Sartobind Q membrane displayed several advantages over a chromatography column prepared with Q Sepharose Fast Flow chromatography resin, referred to as the "Q column," at pH 7.2. For example, the Q membrane permitted a faster flow rate, provided a higher capacity, and provider for an overall faster polishing step. Both the Q membrane and the Q chromatography column provided adequate viral clearance. Additionally, the Q membrane may be loaded with the eluate of a cation-exchange chromatography column pool, following one-fold dilution, having a conductivity of about 6.7 to 6.8 mS/cm after titration to a pH of about 7.2. Since, in many membrane designs, the Q membrane is intended to be used once and then disposed, cleaning validation, column lifetime studies, resin carryover development studies, column storage evaluation studies, and column packing studies needed for Q columns are eliminated from the polishing protocol. Using the Q membrane rather than the Q chromatography column decreased the time expended in the polishing step by one day.

TABLE 1

Utilization of Q Membrane versus a Q Chromatography Column in a Polishing Step

|  | Q Chromatography Column | Q Membrane |
| --- | --- | --- |
| Flux/linear velocity | 100-150 cm/hr | 450-600 cm/hr |
| Capacity | 50-70 g/L | >3000 g/m$^2$ |
| Buffer used | 100% | 5% |
| Operation time | 8-9 hr | 2-2.5 hr |
| Cleaning validation | Yes | Single use |
| Viral clearance | Good | Good |

As identified in one embodiment of the present invention, combining protein-A affinity column chromatography with a first cation-exchange-chromatography polishing step and a second Q-membrane-filtration polishing step provides several advantages. Advantages include: (1) a greater than 85% protein recovery over the entire process; (2) a decrease in processing time by about 1 day; and (3) a decrease in about 50% of the buffer volume used during the polishing process.

Although the present invention has been described in terms of particular embodiments, it is not intended that the invention be limited to these embodiments. Modifications within the spirit of the invention will be apparent to those skilled in the art. For example, in alternate embodiments of the present invention, the buffers used in the equilibration, loading, and elution of the target protein from the chromatography columns and filters may contain one or more additional salts than those listed, and organic solvents may also be present in the buffers and eluants. Additional chromatography columns and purification steps may be employed, including additional cation-exchange chromatography, anion-exchange chromatography, size exclusion chromatography, affinity chromatography, hydroxyapatite chromatography, and hydrophobic interaction chromatography. The sequential purification process may employ any of a large number of different liquid column chromatography systems. The sequential columns may be prepared in-line, or may be physically separated from each other. Although the described embodiments are directed to purification of $F_c$-containing proteins, alternative polishing-step embodiments of the present invention may be employed in purification processes directed to many other types of target molecules.

The foregoing descriptions of specific embodiments of the present invention are presented for purpose of illustration and description. They are not intended to be exhaustive or to limit the invention to the precise forms disclosed. Obviously many modifications and variations are possible in view of the above teachings. The embodiments are shown and described in order to best explain the principles of the invention and its practical applications, to thereby enable others skilled in the art to best utilize the invention and various embodiments with various modifications as are suited to the particular use contemplated. It is intended that the scope of the invention be defined by the following claims and their equivalents:

The invention claimed is:

1. A method for removing residual impurities from a first target-molecule solution, the method comprising:
   loading the target-molecule solution onto a cation-exchange-chromatography column;
   eluting the target molecule as a second target-molecule solution from the cation-exchange-chromatography column using a time dependent pH gradient buffer eluant to remove impurities from the first target molecule solution; and
   passing the second target-molecule, diluted one-fold or less, solution through a Q membrane at a flow rate of between 400 and 600 cm/h to remove residual impurities from the second target-molecule solution.

2. The method of claim 1 wherein the target molecule is an Fc-region-containing protein.

3. The method of claim 1 wherein the target molecule is one of:
   an Fc-containing, naturally occurring antibody;
   an Fc-containing, synthetic antibody; and
   an Fc-containing, recombinant antibody.

4. The method of claim 3 wherein the target molecule is initially purified in an affinity-chromatography capture step comprising:
   loading a target-molecule sample solution onto a chromatography column prepared with a protein-A chromatography resin; and
   eluting the target-molecule in the first target-molecule solution from the chromatography column.

5. The method of claim 1 wherein the second target-molecule solution is diluted one-fold prior to applying the second target-molecule solution to the membrane.

6. The method of claim 1 wherein residual impurities may include one or more of:
   host-cell proteins;
   host DNA;
   viral DNA;
   host RNA;
   viral RNA;
   target-molecule aggregates;
   viral fragments;
   intact viruses; and
   endotoxins.

7. The method of claim 1 wherein the membrane passes neutral or positively charged molecules with smallest dimensions less than a threshold length, while retaining negatively charged molecules and molecules with a smallest dimension greater than a threshold length.

8. A method for removing residual impurities selected from the from consisting of host-cell proteins, DNA, RNA, antibody aggregates, virus particles, virus fragments, and endotoxins from an antibody solution initially purified in an affinity-chromatography capture step, the method comprising:
   loading the antibody solution onto a cation-exchange-chromatography column;
   eluting the antibody as a second antibody solution from the cation-exchange-chromatography column using a time dependent pH gradient buffer eluant to remove residual impurities from the antibody solution; and
   passing the second antibody solution, diluted one-fold or less, through a selectively permeable Q membrane, at a flow rate of between 400 and 600 cm/h to remove the residual impurities from the second antibody solution while passing between 95% and 100% of natively folded and non-aggregated antibody into a resultant, purified antibody solution.

* * * * *

UNITED STATES PATENT AND TRADEMARK OFFICE
CERTIFICATE OF CORRECTION

PATENT NO. : 7,662,930 B2  Page 1 of 1
APPLICATION NO. : 11/635800
DATED : February 16, 2010
INVENTOR(S) : Joe Xin Hua Zhou It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 139 days.

Signed and Sealed this

Twenty-eighth Day of December, 2010

David J. Kappos
*Director of the United States Patent and Trademark Office*